US010564101B1

(12) United States Patent
Néron et al.

(10) Patent No.: US 10,564,101 B1
(45) Date of Patent: Feb. 18, 2020

(54) CABLE MOVEMENT-ISOLATED MULTI-CHANNEL FLUORESCENCE MEASUREMENT SYSTEM

(71) Applicant: Optomak, Inc., Quebec (CA)

(72) Inventors: Jean-Luc Néron, Quebec (CA); Olivier Dupont-Therrien, Quebec (CA); Harold Dehez, Quebec (CA)

(73) Assignee: OPTOMAK, INC. (CA)

( * ) Notice: Subject to any disclaimer, the term of this patent is extended or adjusted under 35 U.S.C. 154(b) by 0 days.

(21) Appl. No.: 16/179,254

(22) Filed: Nov. 2, 2018

(51) Int. Cl.
*G02B 6/36* (2006.01)
*G01B 9/02* (2006.01)
*G01N 21/64* (2006.01)
*G02B 6/42* (2006.01)

(52) U.S. Cl.
CPC ..... *G01N 21/6428* (2013.01); *G01B 9/02091* (2013.01); *G02B 6/3604* (2013.01); *G02B 6/4246* (2013.01); *G01N 2021/6441* (2013.01); *G01N 2201/068* (2013.01); *G01N 2201/0853* (2013.01)

(58) Field of Classification Search
CPC ............... G02B 6/3604; G02B 6/4246; G01B 9/02091; G01N 21/6428; G01N 2021/6441; G01N 2201/068; G01N 2201/0853
USPC ...................................................... 250/459.1
See application file for complete search history.

(56) References Cited

U.S. PATENT DOCUMENTS

| | | |
|---|---|---|
| 4,643,521 A | 2/1987 | Harstead et al. |
| 4,725,116 A | 2/1988 | Spencer et al. |
| 5,304,173 A * | 4/1994 | Kittrell .............. A61B 1/00096 600/477 |
| 5,693,043 A * | 12/1997 | Kittrell .............. A61B 1/00096 606/15 |
| 7,515,782 B2 | 4/2009 | Zhang et al. |
| 7,613,371 B2 | 11/2009 | Ankerhold |
| 7,881,569 B2 | 2/2011 | Zhang et al. |
| 8,380,024 B1 | 2/2013 | Zhang et al. |
| 8,781,560 B2 * | 7/2014 | Bambot ............... A61B 5/0059 600/473 |

(Continued)

OTHER PUBLICATIONS

Ghosh, et al., "Miniaturized integration of a fluorescence microscope", Nature Methods, vol. 8, No. 10, Oct. 2011, pp. 1-12 (12 pages in pdf), Nature America, Inc., US.

(Continued)

*Primary Examiner* — Taeho Jo
(74) *Attorney, Agent, or Firm* — Mitch Harris, Atty at Law, LLC; Andrew M. Harris

(57) ABSTRACT

A multi-site fluorescence recording system provides simultaneous monitoring of cell activity in different brain regions of a freely moving animal. The system includes an electrical rotary joint that couples signals to and from an external data acquisition and control unit connected to a stator of the rotary joint, which releases twisting of the optical fibers connected to the animal. Electrical signals are coupled to one or more fluorescence stimulation/detection units on the rotor of the rotary joint. The fluorescence stimulation/detection units receive one or more connections from optical fibers that connect the stimulation/detection unit(s) to the different brain sites. The rotating stimulation/detection units include spectral filters to separate the excitation light from the fluorescence signal, light sensors (an image sensor or photodiodes) and excitation light sources.

28 Claims, 14 Drawing Sheets

(56) References Cited

U.S. PATENT DOCUMENTS

| | | |
|---|---|---|
| 8,826,973 B2 | 9/2014 | Moxley et al. |
| 9,046,659 B2 | 6/2015 | Doric |
| 9,207,405 B2 | 12/2015 | Doric |
| 9,357,923 B2 | 6/2016 | Courtney et al. |
| 9,791,683 B2 | 10/2017 | Doric et al. |
| 2002/0045811 A1* | 4/2002 | Kittrell ............... A61B 1/00096 600/407 |
| 2004/0007675 A1* | 1/2004 | Gillispie ............... G01J 3/4406 250/458.1 |
| 2010/0076304 A1* | 3/2010 | Teramura ............... A61B 3/102 600/425 |
| 2012/0232404 A1* | 9/2012 | Bambot ............... A61B 5/0059 600/476 |
| 2012/0323112 A1* | 12/2012 | Jokerst ................. A61K 49/225 600/420 |
| 2015/0160125 A1* | 6/2015 | Jackson ................. G01N 21/59 250/227.23 |
| 2015/0238135 A1* | 8/2015 | Bambot ............... A61B 5/0059 600/476 |
| 2015/0272445 A1* | 10/2015 | Rozental .............. A61B 5/0071 600/407 |
| 2018/0228375 A1* | 8/2018 | Kim ...................... G01N 33/582 |
| 2018/0259317 A1* | 9/2018 | Tearney ............. G01B 9/02091 |
| 2018/0348439 A1* | 12/2018 | Yamada ............. G01B 9/02091 |

OTHER PUBLICATIONS

Gunaydin, et al., "Natural Neural Projection Dynamics Underlying Social Behavior", Cell, 157, Jun. 2014, pp. 1-27 (27 pages in pdf), Elsevier Inc., US.

Kim, et al., "Simultaneous fast measurement of circuit dynamics at multiple sites across the mammalian brain", Nature Methods, Advance Online Publication, Feb. 2016, pp. 1-8 (8 pages in pdf), Nature America, Inc., US.

Doric Lenses, "Neuroscience Hardware Catalog v9.6" downloaded from http://www.doriclenses.com/downloads/Product_catalog_RELEASE_WEB.pdf on Oct. 24, 2018, 181 pages (pp. 1-181 in pdf).

* cited by examiner

CABLE MOVEMENT-ISOLATED MULTI-CHANNEL FLUORESCENCE MEASUREMENT SYSTEM

BACKGROUND OF THE INVENTION

1. Field of the Invention

The present invention relates to the fields of spectroscopy and fluorescence recording, and in particular to a multi-channel fluorescence measurement system having fluorescence stimulation/detection units incorporated at the rotor of an electrical rotary joint for in vivo fluorescence recording in biological tissue for biomedical research applications.

2. Background of the Invention

Fiber photometry is an optical technique initially developed for neuroscience applications to record the activity of a specific population of neurons in behaving animals (e.g. brain activity). To become light sensitive, brain tissue is labeled with genetically encoded functional fluorescent proteins (e.g., Calcium indicators) that have fluorescence emissions which are modulated by activity of the labeled cells.

In contrast to miniaturized epi-fluorescence microscopy designed for activity monitoring of single cells, spatial resolution of fiber photometry is typically limited by the diameter of the optical fiber cable used to perform the measurement. A typical signal in fiber photometry provides a sum of the activity of hundreds of cells located close to the tip of a fiber optic implant. Early fiber photometry systems were developed to record a single brain region connected to a single optical fiber cable, and typically use photodiodes to perform measurements. When making measurements on freely moving animals, optical rotary joints are used to prevent twisting of the optical fiber cable and to reduce stress on the animal that would otherwise be caused by the pulling/twisting of the cable. In order to simultaneously record the fluorescence activity of multiple brain regions, proposed solutions use an image sensor in place of the photodiodes to image the output of several optical fibers cable that are connected to different brain regions.

However, both the existing and proposed solutions described above are limited, in that using an optical rotary joint induces signal fluctuations caused by the rotation and limits the system to two optical cables when a two-channel optical rotary joint is used, limiting the measurement to two brain regions. In the proposed image sensor solution, single channel or two-channel optical rotary joints cannot be used to transfer an optical image, so the rotary joints are not compatible with available systems for multiple site recording that use an image sensor as a detector.

Therefore, it would be desirable to provide a multi-channel fluorescence measurement system that can provide multiple simultaneous fluorescence measurements of brain regions, while releasing cable twisting when the animal is freely behaving.

SUMMARY OF THE INVENTION

The above objectives, as well as other improvements, are achieved in an optical measurement system for performing fluorescence measurements, a rotary joint and a method of performing fluorescence measurements. The rotary joint is a rotary joint forming part of the optical measurement system and the method is a method of operation of the optical measurement system.

The optical measurement system performs multiple fluorescence measurements at multiple distinct regions within a moving sample, and includes a plurality of optical fibers having first ends coupled to the moving sample. The optical system also includes an electrical rotary joint including a rotor and a stator. The rotor includes at least one optical connection for receiving second ends of the optical fibers, and at least one fluorescence stimulation/detection unit coupled to the optical connection(s) for introducing excitation light to the plurality of optical fibers and receiving returning fluorescence light from the plurality of optical fibers. The stimulation/detection units include at least one optical filter optically coupled to the connection(s) for separating the returning fluorescence light from the excitation light, at least one light source for providing the excitation light, and at least one electro-optical detector coupled to the optical connection(s) for detecting the returning fluorescence light. An output of the electro-optical detector(s) is coupled from the rotor to the stator of the rotary joint, and the stator provides at least one electrical output for providing electrical connection to the at least one electro-optical detector and power for the light source is also coupled through the electrical rotary joint. The optical measurement system also includes a data acquisition unit with one or more electrical detection inputs coupled to the electrical output(s) of the stator of the electrical rotary joint for recording an output of the electro-optical detector(s) and an output for controlling power supplied to the input of the at least one light source.

The connection from the optical fibers may be a single bundled connection of the second ends of the optical fibers, and the electro-optical detector may use an image sensor to image the ends of the optical fibers to produce measurements of the returning fluorescence emission from each fiber. Alternatively, the connection from the optical fibers may be a corresponding plurality of connections, with multiple electro-optical detectors included in or on the rotor to perform individual measurements of the returning fluorescence emission from each fiber.

The foregoing and other objectives, features, and advantages of the invention will be apparent from the following, more particular, description of the preferred embodiment of the invention, as illustrated in the accompanying drawings.

BRIEF DESCRIPTION OF THE DRAWINGS

The novel features believed characteristic of the invention are set forth in the appended claims. The invention itself, however, as well as a preferred mode of use, further objectives, and advantages thereof, will best be understood by reference to the following detailed description of an illustrative embodiment when read in conjunction with the accompanying drawings, wherein like reference numerals indicate like components, and:

DESCRIPTION OF ILLUSTRATED EMBODIMENT

The present disclosure provides examples of photometry systems for simultaneous monitoring of cell activity in different regions, e.g., brain, spinal cord, muscles, etc., in freely behaving animals, e.g., rodents or monkeys. To monitor the different regions simultaneously, an optical fiber cable is connected to each region of the sample and relays the fluorescence signal from the sample to the light detector, as well as providing excitation light to the sample regions. The optical fibers are connected to the rotor of an electrical rotary joint that releases cable twisting when the animal is freely behaving. Two distinct example embodiments are disclosed herein. In one embodiment, the proximal ends of all the optical fiber cables are combined and imaged on a single image sensor (e.g. CCD, CMOS, . . . ) to simultaneously monitor the activity of all the sites. Only one set of optical filters is required and the number of recording sites is only limited by the number of optical fibers that can be imaged within the field of view of the system.

In another embodiment, the fluorescence signal returning from multiple optical fibers is individually detected by a corresponding photo-detector, e.g., a photodiode, phototransistor or photomultiplier tube (PMT). The photo-detectors are synchronized to simultaneously record the activity of all of the brain regions. In the instant configuration, one set of optical filters is required for each optical fiber.

In both of the disclosed embodiments, to release twisting of the optical fiber connected to the animal, a rotor of an electrical rotary joint incorporates the fluorescence detection/stimulation unit(s) that provide the excitation light and detect the returning fluorescence emission light. The rotor conveys electrical signals to and from the stator of the rotary joint, which is connected to a data acquisition and control unit. Free rotation is essential for multi-brain-site measurements where multiple optical fiber cables are connected to a moving sample. The rotary joint may be passive or may be torque-assisted. In a passive mode or in passive implementations, the rotor passively follows the movement of the animal using low friction bearings and low friction electrical contacts. To ensure sufficient electrical conductivity, the electrical contacts will necessarily introduce friction, which will produce resistance to rotation that is difficult to overcome for small rodents, such as mice. Therefore, in an active mode or an active implementation, a torque-assisted electrical rotary joint is provided, in which a torque sensor detects a torque applied to the rotor by the animal and triggers motor-assisted rotation. The active mode/implementation is particularly suitable for use with animals of small weight, such as mice.

Figure 1A:
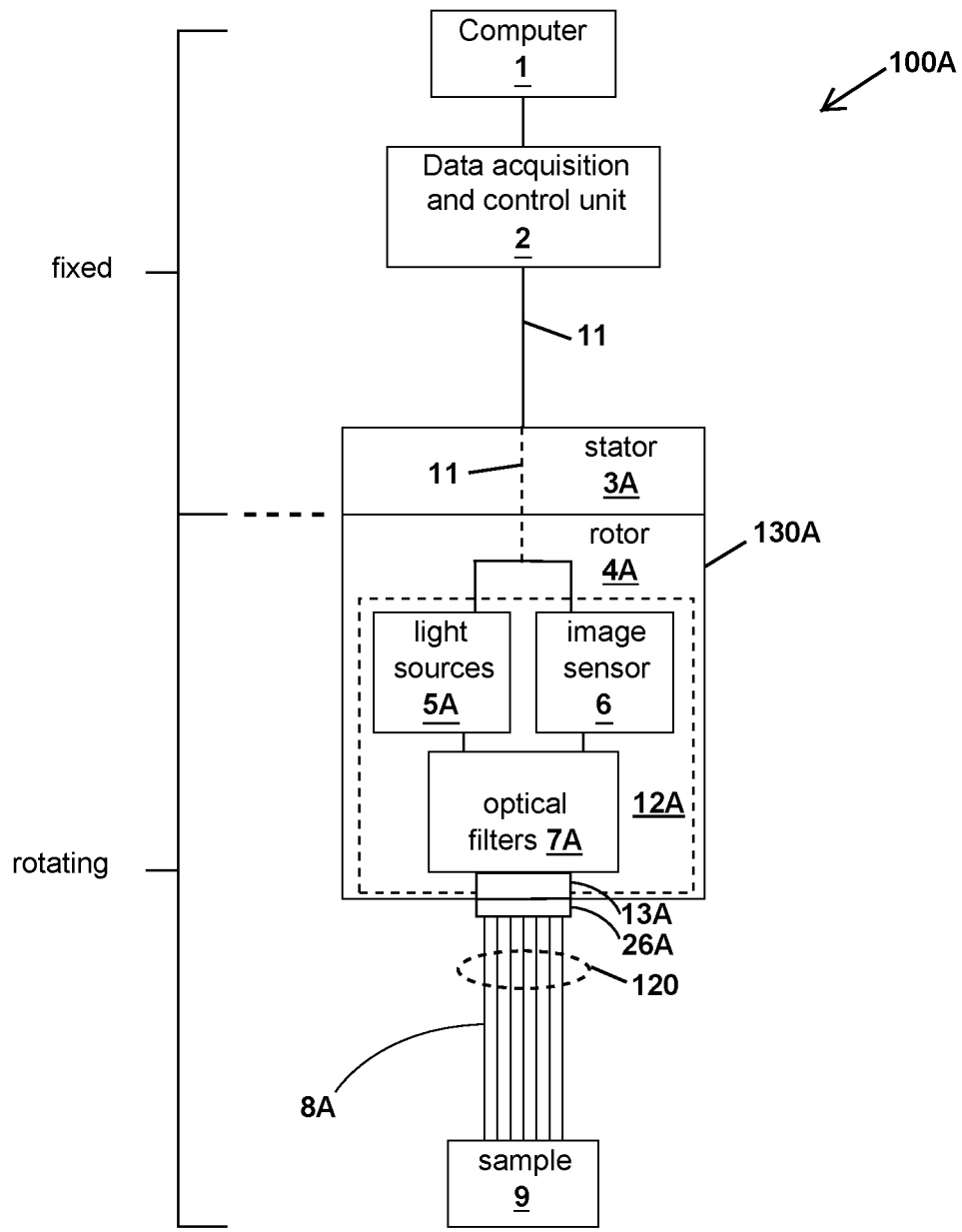
FIG. 1A is a block diagram of an example optical measurement system 100A in accordance with an embodiment of the disclosure.

Referring now to FIG. 1A, an example optical measurement system 100A is shown, in accordance with an embodiment of the disclosure. Optical measurement system 100A is a fiber photometry system for measuring fluorescence emissions returning from multiple regions within a sample 9 over multiple fiber optic cables 8A, which may be single or multi-core. First (distal) ends of fiber optic cables 8A are inserted into different regions of sample 9, or are connected to further optical probes inserted into different regions of sample 9, via connections at the distal ends thereof. Fiber optic cables 8A conduct excitation light at one or more frequencies that stimulate fluorescence emissions from the different regions of sample 9, as well as returning the light produced by the fluorescence emissions. Fiber optic cables 8A are connected at their proximal ends via a connector 26A that receives an optical cable bundle 120 that combines fiber optic cables 8A mechanically, so that an image produced by the exit profile of optical cable bundle 120 is a composite image of the individual second ends of fiber optic cables 8A, which correspond to different areas of the resulting image. Connector 26A is connected to a corresponding connector 13A of a fluorescence stimulation/detection unit 12A, which is a module mounted on or provided internal to a rotor 4A of an electrical rotary joint 130A. Fluorescence stimulation/detection unit 12A includes a set of optical filters 7A that serve as a diplexer to separate stimulation light from the returning fluorescence light produced by sample 9, as well as providing narrowband filtering to improve reception of the returning fluorescence light. Fluorescence stimulation/detection unit 12A also includes one or more light sources 5A, e.g., light-emitting diodes (LEDs) or laser diodes, that generate excitation light at the excitation wavelength(s) and provide the excitation light through optical filters 7A to fiber optic cables 8A. Fluorescence stimulation/detection unit 12A also includes an image sensor 6 that captures the composite image provided by the exit profile of optical cable bundle 120 at connector 13A, with each of fiber optic cables 8A corresponding to a different area of the image captured by image sensor 6.

In order to prevent twisting of fiber optic cables 8A and resulting extraction of probes from sample 9 or other harm to sample 9 and/or the measurements, image data and control signals 11 are electrically coupled between rotor 4A and a stator 3A of electrical rotary joint 130A. The image data includes a representation of the composite image of the fluorescence emissions captured by fiber optic cables 8A, with individual areas of the image corresponding to individual ones of fiber optic cables 8A. The intensity within each of the areas are then averaged with a weighting function to produce an intensity result for each of fiber optic cables 8A over time. The collection and averaging of the image sensor data is performed by a computer 1 coupled to a data acquisition and control unit 2, or alternatively, a portion or all of the weighting can be performed within data acquisition and control unit 2, with computer 1 collecting and further processing the resulting output of data acquisition and control unit 2. Computer 1 executes dedicated software that can be synchronized with other components via analog and/or digital inputs/outputs of data acquisition and control unit 2. The software features a graphic interface to synchronize data acquisition operations and to specify parameters of recording and light control as performed by optical measurement system 100A.

Figure 1B:
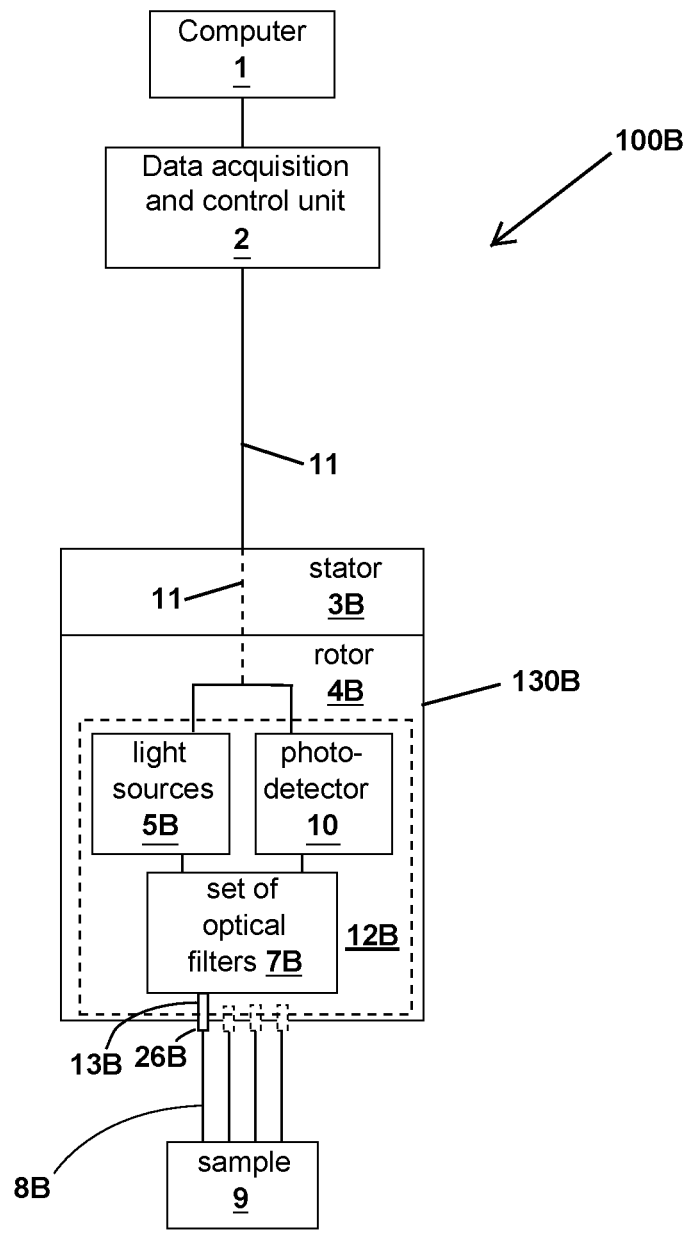
FIG. 1B is a block diagram of another example optical measurement system 100B in accordance with another embodiment of the disclosure.

Referring now to FIG. 1B, an example optical measurement system 100B is shown, in accordance with another embodiment of the disclosure. Example optical measurement system 100B is similar to example optical measurement system 100A described above, so only differences between the two embodiments will be described below. In example optical measurement system 100B, fiber optic cables 8B are not bundled, but are rather connected to multiple individual fluorescence stimulation/detection units 12B incorporated in or on an electrical rotary joint 130B. A single example of fluorescence stimulation/detection units 12B is illustrated in FIG. 1B, for clarity. Fluorescence stimulation/detection units 12B is connected to fiber optic cables 8B by individual connectors 26B and corresponding individual connectors 13B, one for each of fluorescence stimulation/detection units 12B. Fluorescence stimulation/detection units 12B include light sources 5B and optical filters 7B, which perform the same functions as described above with reference to FIG. 1A as light sources 5A and optical filters 7A. However, each of fluorescence stimulation/detection units 12B includes a set of light sources 5B and optical filters 7B for excitation and measurement of a single region within sample 9, and a photo-detector 10, e.g., a photodiode, phototransistor or PMT is used to measure the returning fluorescence light returned by the corresponding one of fiber optic cables 8B. Output signals from photo-detector 10 and control signals for operating light sources 5B are coupled from a rotor 4B of electrical rotary joint 130B to a stator 3B and are sent to data acquisition and control unit 2 and to computer 1 for further processing.

Figure 2A:
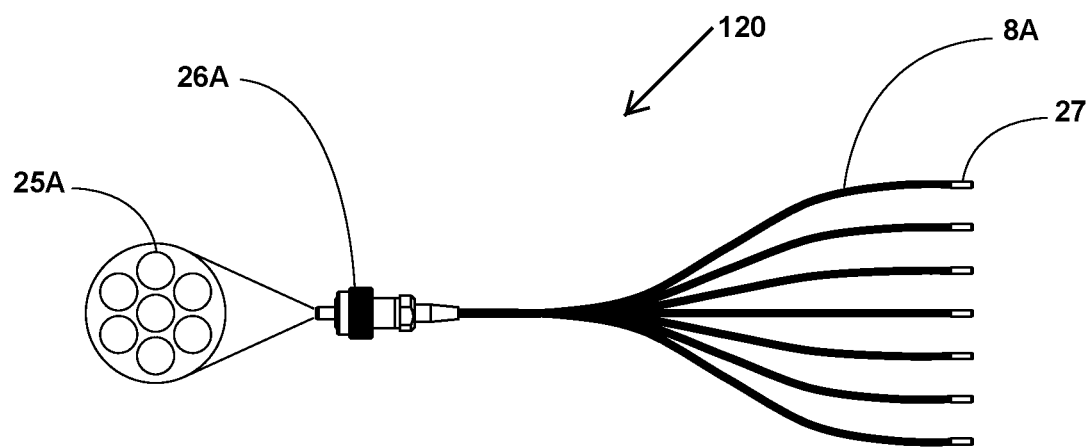
FIG. 2A is a pictorial diagram depicting an example optical cable bundle 120 of optical measurement system 100A depicted in FIG. 1A.

Referring now to FIG. 2A, an example optical cable bundle 120 is shown, as may be used in optical measurement system 100A of FIG. 1A. Individual fiber optic cables 8A are connected to the animal, i.e., coupled to probes within the animal, with miniature optical connectors 27, e.g., ferrules and sleeves. A more robust connector type, e.g., FC-PC or SMA optical connectors is used as connector 26A which connects to connector 13A in optical measurement system 100A of FIG. 1A and which combines the individual cores of fiber optic cables 8A as shown in an interface 25A, which produces the image received by fluorescence stimulation/detection unit 12A, and also receives a uniform illumination by the excitation light, as will be described in further detail below. The use of miniature optical connectors 27 and connector 26A provides optical connection repeatability and easy replacement of fiber optic cables 8A. The cores of fiber optic cables 8A are in the range from 10 μm to 1 mm, and the numerical aperture is above 0.20 for light collection efficiency.

Figure 2B:
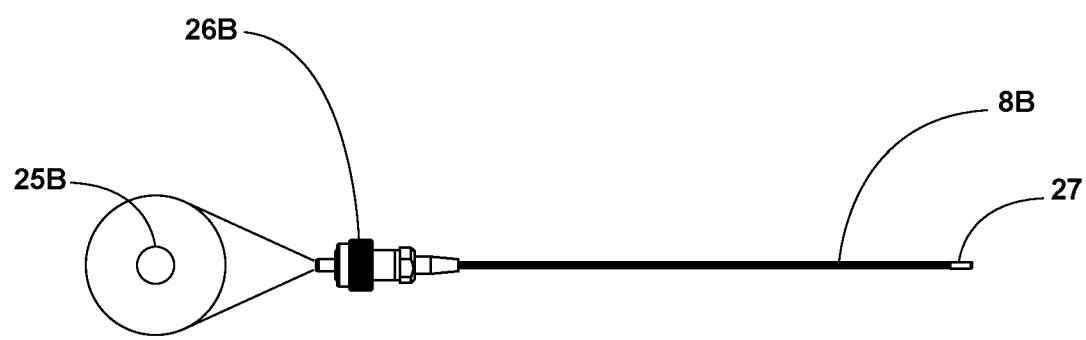
FIG. 2B is a pictorial diagram depicting an example fiber optic cable 8B of optical measurement system 100B depicted in FIG. 1B.

Referring now to FIG. 2B, an example fiber optic cable 8B is shown, as may be used in optical measurement system 100B of FIG. 1B. Individual fiber optic cables 8B are connected to the animal, i.e., coupled to probes within the animal, with miniature optical connectors 27, e.g., ferrules and sleeves. A more robust connector type, e.g., FC-PC or SMA optical connectors are used as connector 26B, which provides individual interfaces 25B, one at the end of each of multiple fiber optic cables 8B, which are connected to corresponding connectors 13B in optical measurement system 100B of FIG. 1B. As in optical cable bundle 120 of FIG. 2A, the cores of fiber optic cables 8B are in the range from 10 μm to 1 mm, and the numerical aperture is above 0.20 for light collection efficiency.

Figure 3:
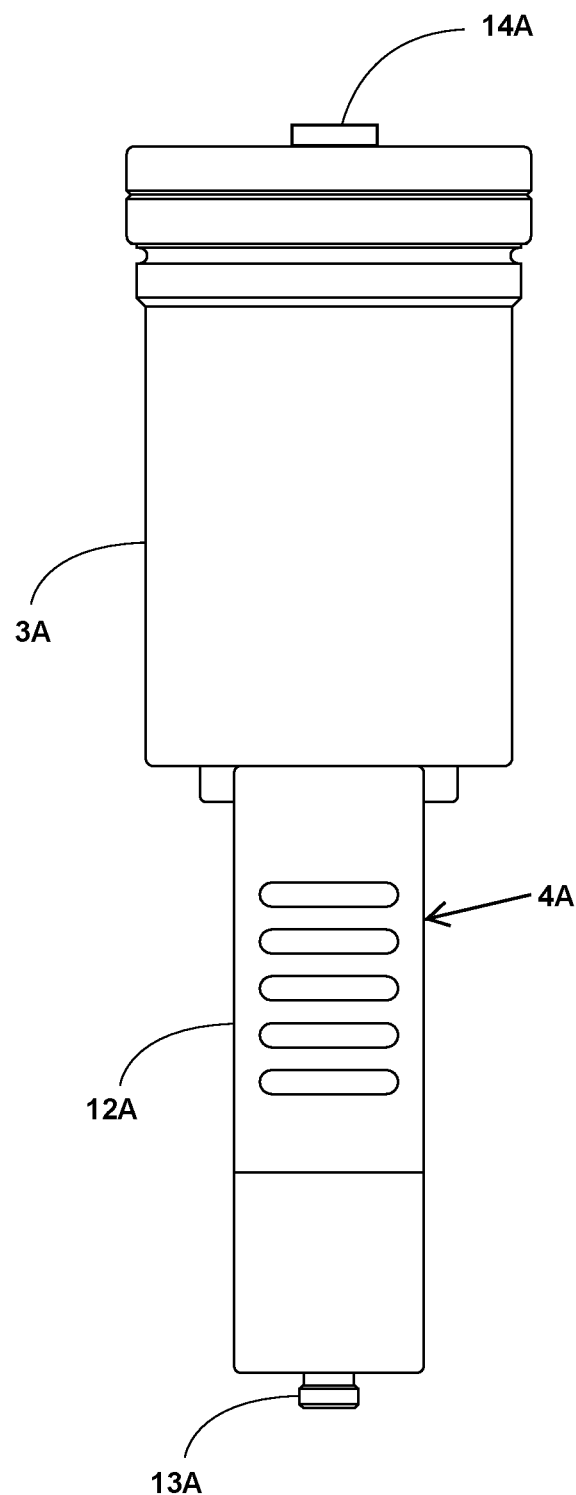
FIG. 3 is a side view of an example electrical rotary joint 130A of optical measurement system 100A depicted in FIG. 1A.
Figure 4:
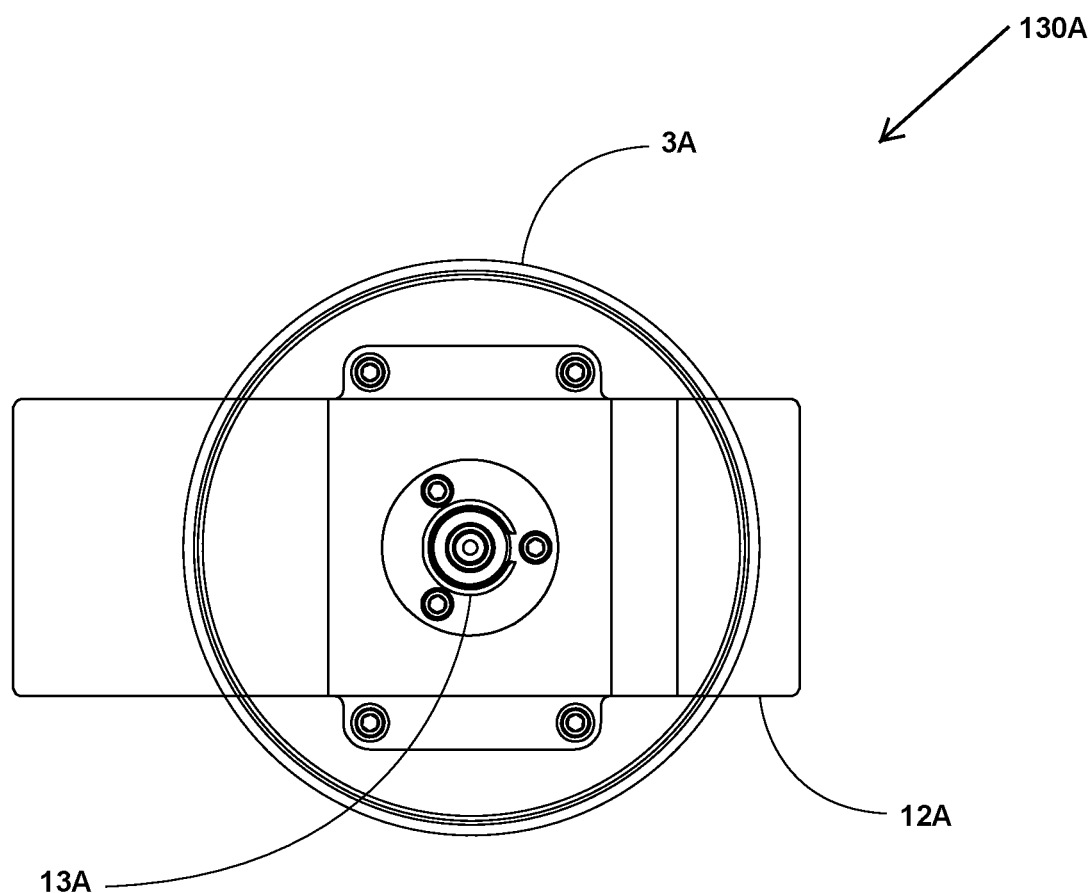
FIG. 4 is a bottom view of example electrical rotary joint 130A of FIG. 3.

Referring now to FIG. 3 and FIG. 4, a side view and a bottom view, respectively, of electrical rotary joint 130A of optical measurement system 100A of FIG. 1A are shown. The positions of rotor 4A and stator 3A are shown, and rotor 4A is rotationally coupled to stator 3A with a low-friction bearing and electrical interconnects. Electrical connections 14A are provided on stator 3A for connection to data acquisition and control unit 2 of FIG. 1A. Fluorescence stimulation/detection unit 12A is mounted to, or forms the body of rotor 4A, which includes connector 13A for attachment of connector 26A of optical cable bundle 120 of FIG. 2A. By providing fluorescence stimulation/detection units 12A as modules mounted to rotor 4A, fluorescence stimulation/detection units 12A can be interchanged for other fluorescence stimulation/detection units 12A having different excitation and detection capabilities. For example fluorescence stimulation/detection units 12A having different illumination sources and illumination/detection pathway filter wavelengths, or different numbers of detection and/or illumination features, as will be described for different applications below. The interchangeability provides compatibility with a multitude of fluorescent proteins having different excitation and emission spectra.

Figure 5A:
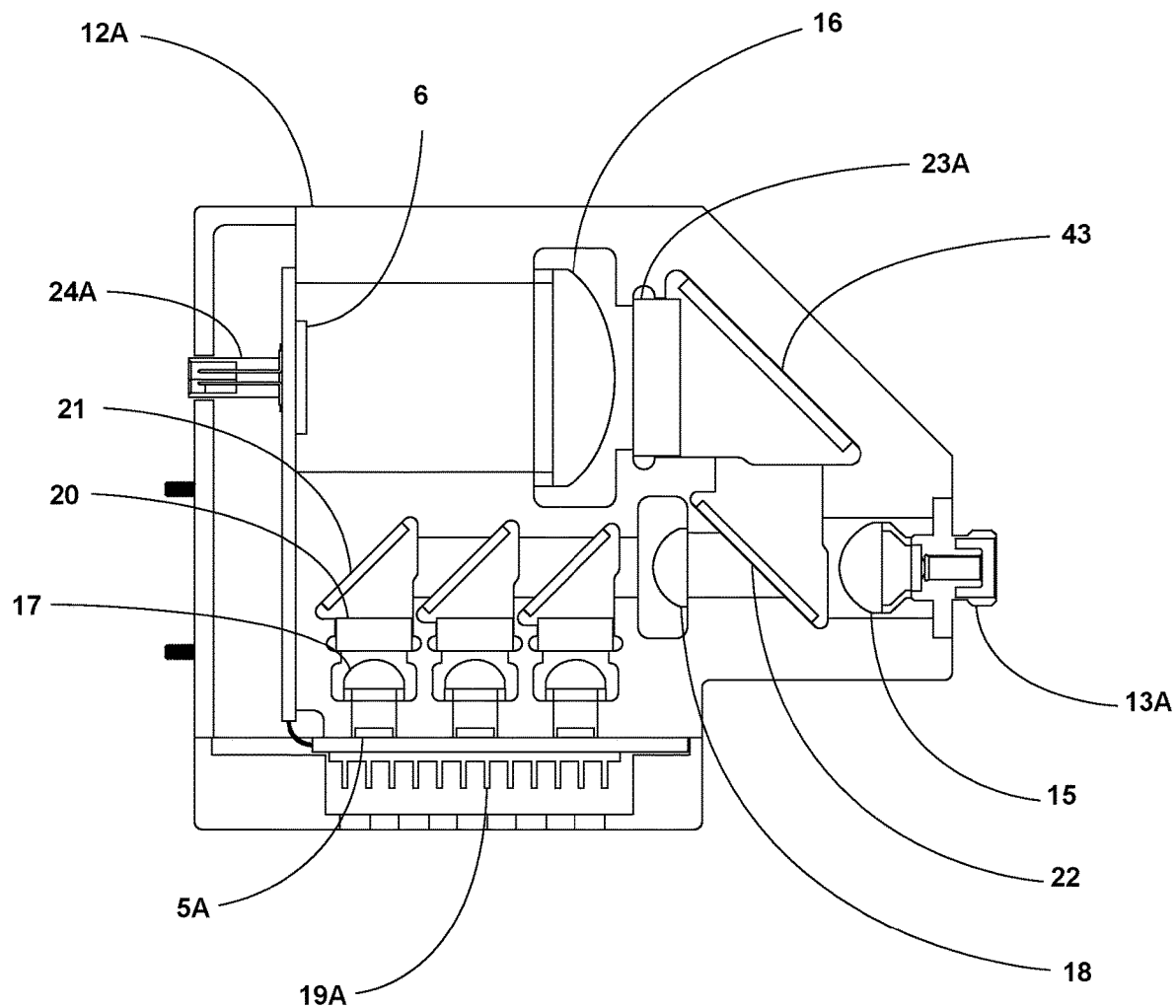
FIG. 5A is a side cut-away view of a fluorescence stimulation/detection unit 12A of electrical rotary joint 130A of FIG. 3 and FIG. 4.
Figure 6A:
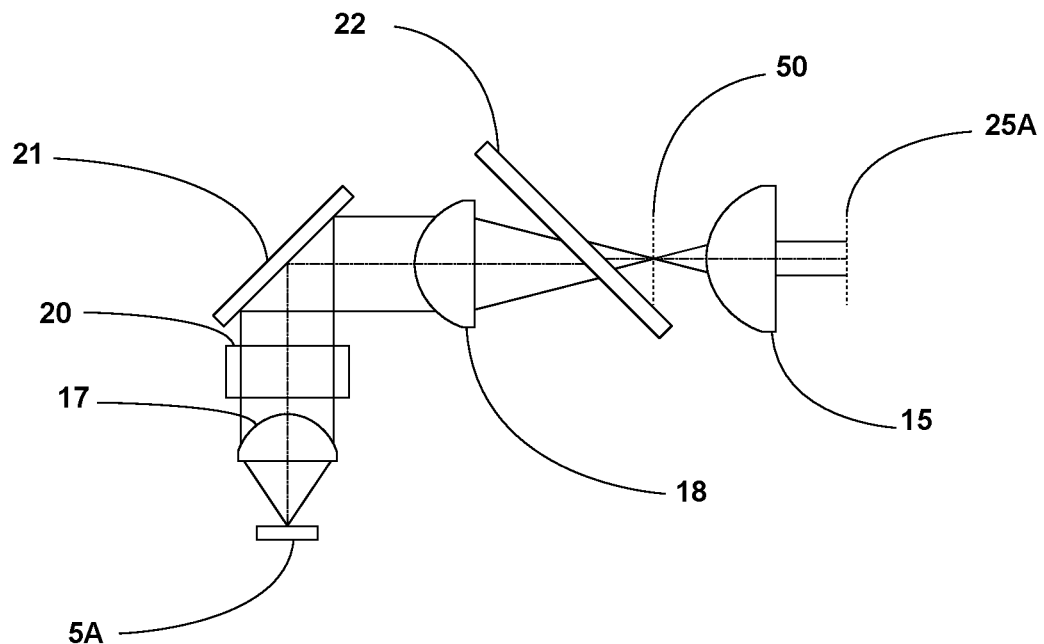
FIG. 6A is a pictorial diagram depicting an illumination pathway within fluorescence stimulation/detection unit 12A of FIG. 5A.

Referring now to FIG. 5A, a cut-away side view of fluorescence stimulation/detection unit 12A is shown, illustrating details of the optical and electrical components within. Connector 13A, which receives connector 26A of optical cable bundle 120 of FIG. 2A and interface 25A thereby, is optically coupled by an objective lens 15. Excitation light is provided by light sources 5A, e.g., LEDs or laser diodes, for fluorescence protein excitation. Inclusion of light sources 5A in fluorescence stimulation/detection unit 12A and thus on rotor 4A of electrical rotary joint 130A ensures excitation signal stability, since only electrical control signals and power sources that operate light sources 5A pass through electrical rotary joint 130A, and not the excitation illumination beams. An electrical connector 24A provides for electrical connections between rotor 4A and fluorescence stimulation/detection unit 12A, providing power/control for light sources 5A, as well as an interface to image sensor 6 within fluorescence stimulation/detection unit 12A. Since optical power requirements for fiber-photometry measurement are low, the heat produced by light sources 5A is also low and the heat can be dissipated passively with a passive heat sink 19A. If higher thermal dissipation is required, a fan may be included to move air over the fins of heat sink 19A. To deliver excitation light to all the brain regions with the same optical parameters (light intensity and angular distribution), fluorescence stimulation/ detection unit 12A is configured to generate a uniform illumination over the total field of view at the object plane located at the proximal end of the optical fibers of fiber optic cable 8A, i.e., at interface 25A shown in FIG. 2A. As illustrated in FIG. 6A, to which additional reference is made, in order to accomplish the above, each of light sources 5A is imaged at the back focal plane 50 of objective lens 15. FIG. 6A depicts the individual illumination pathway from each of light sources 5A to interface 25A of fiber optic cable 8A of FIG. 1A. Imaging light sources 5A at back focal plane 50 ensures that each of fiber optic cables 8A are illuminated with the same angular distribution, and discontinuities at the surface of light sources 5A are not imaged in the object plane. In the depicted embodiment, to improve filtering efficiency by reducing the angle of incidence on an excitation bandpass filter 20 and dichroic beamsplitter, the output of each of light sources 5A is first collimated by an aspheric lens 17 before the collimated beams pass through excitation bandpass filter 20 and dichroic beamsplitter 21. Then, another lens 18, e.g., a plano-convex, aspheric, or achromatic lens positioned before the back focal plane of objective lens 15, focuses the collimated beam at back focal plane 50 of objective lens 15, resulting in uniform illumination across interface 25A of FIG. 2A that combines the fibers of fiber optic cables 8A.

To receive returning fluorescence light from the samples, in the example embodiment, objective lens 15 further generates a magnified image of the object plane with a fixed tube length, with no tube lens required. In order to minimize the exterior dimensions of the system and also to optimize aberration correction, a high numerical aperture aspheric lens is used for objective lens 15. In the example, the numerical aperture of objective lens 15 is between 0.20 and 0.80. In another embodiment, objective lens 15 is infinity-corrected and a tube lens 16, e.g., a plano-convex lens, aspheric lens, or achromatic lens, is inserted after dichroic beamsplitter 22 and a mirror 43 before reaching image sensor 6 in order to adjust the magnification and reduce the angular divergence of the returning fluorescence light at the surface of a single-band emission filter 23A and dichroic beamsplitter 22, thereby improving their efficiency. Single-band emission filter 23A removes stray light coming from excitation light reflections within fluorescence stimulation/detection unit 12A. In yet another embodiment, the aspheric lens is replaced by a 4X to 20X high numerical aperture infinity-corrected microscope objective for better correction of optical aberrations (chromatic aberration, spherical aberration, field curvature, and the like). Fluorescence stimulation/detection unit 12A is configured to image a field of view of up to 3 mm×3 mm on image sensor 6, e.g., a CMOS or CCD sensor, with 1 to 10× magnification. The size of the field of view limits the number of brain regions that can be monitored simultaneously. In interface 25A of FIG. 2A, the proximal end of seven optical fibers 400 microns in diameter are imaged simultaneously.

In fluorescence stimulation/detection unit 12A as illustrated in FIG. 5A, three sets of excitation bandpass filter 20 and dichroic beamsplitter 21 are included that form a primary filter set that combine the excitation illumination in the excitation optical pathway. However, the number of excitation sources, i.e., light sources 5A may be from a single light source 5A up to the limits of module size that can be provided on rotor 4A and any degradation of the excitation illumination pathway through the multiple dichroic beamsplitters 21. The primary filter set is configured to combine one, two or three light sources 5A. The primary filter set features: an individual excitation bandpass filter 20 for each light source 5A that reduces the spectral bandwidth of the illumination lights, and an individual dichroic beamsplitter 21 for each light source 5A to combine two or three bands of excitation lights in a single excitation pathway. A secondary filter set separates the one, two or three bands of fluorescence signals emitted by the sample from one, two or three bands of excitation lights. The secondary filter set varies according to number and type of fluorescent markers to be detected.

In one example embodiment, the returning fluorescence measurement signal of one fluorescent protein is detected by image sensor 6, and one light source 5A is used for excitation. In such a configuration, the secondary filter set includes a first dichroic beamsplitter 22 that separates the fluorescence signals from the excitation, and single-band emission filter 23A. For example, GCaMP6 fluorescent proteins having an emission wavelength of approximately 515 nm may be excited by an illumination wavelength of approximately 480 nm. In another embodiment, designed for genetically encoded calcium indicators, a second light source around the isosbestic calcium independent wavelength of the calcium indicator can be added in the system for control measurements. By subtracting the calcium-independent signal from the calcium dependant signal of the calcium indication, motion artifacts can be removed. For example, a second excitation light source at the isosbestic wavelength of the calcium indicator is added to the system for control measurements, e.g., approximately 405 nm for GCaMP6.

Figure 7A:
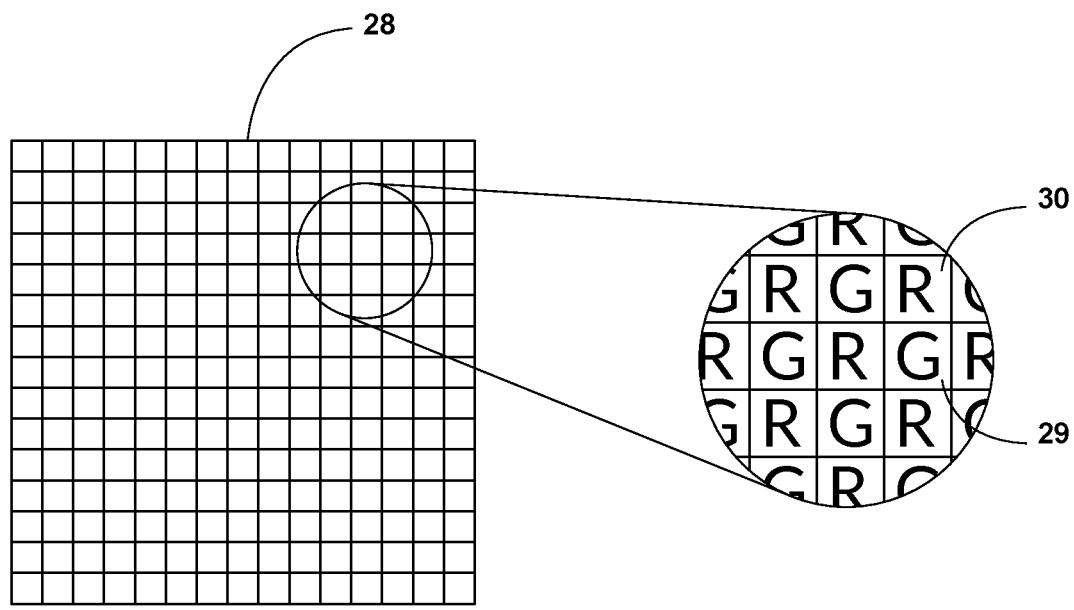
FIG. 7A is a pictorial diagram depicting an example of a patterned optical filter that may be used in fluorescence stimulation/detection unit 12A of FIG. 5A for multi-color imaging.
Figure 7B:
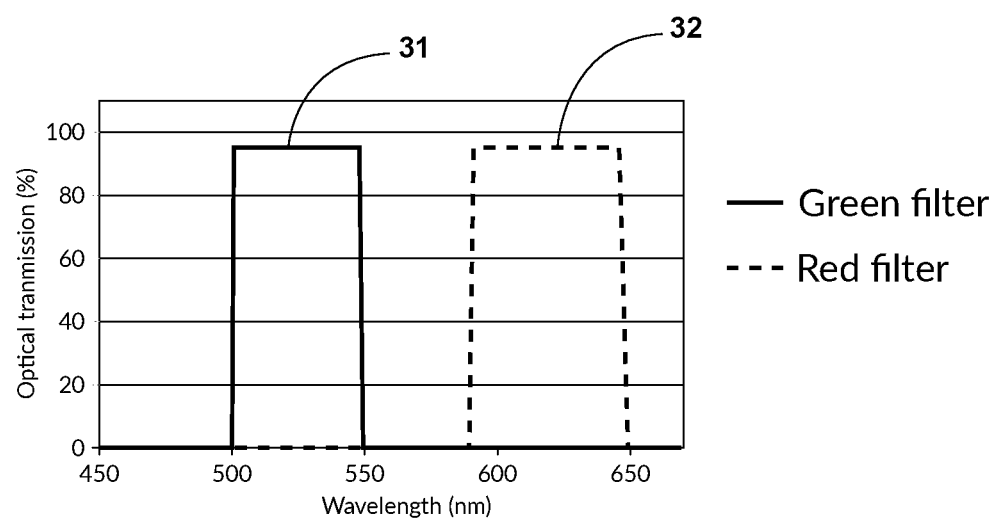
FIG. 7B is a graph depicting the transmission spectra of a patterned optical filter that may be used in fluorescence stimulation/detection unit 12A of FIG. 5A for multi-color imaging.

In another example of a multi-color configuration, the fluorescence signal of two fluorescent proteins are recorded simultaneously on image sensor 6. In the example configuration, a first dichroic beamsplitter 22 separates the fluorescence signals from the excitations, and a dual-band bandpass filter is inserted in place of single-band emission filter 23A, and is designed to pass the fluorescence from the two fluorescent markers is inserted in front of the image sensor 6 and removes stray excitation light from excitation light reflections within fluorescence stimulation/detection unit 12A. In one embodiment, to separate the fluorescence signal from each marker and as shown in FIG. 7A, a matrix 28 of interleaved micro single-band-pass filters 29,30 is inserted in front of image sensor 6 and aligned with the pixels of image sensor 6. FIG. 7B illustrates transmission bands 31,32 of the two sets of micro single-band-pass filters 29,30 that are centered on the fluorescence emission wavelengths of the two detected fluorescent markers. The dimension of micro single-band-pass filters 29,30 is a multiple of the pixel size of the sensor (1× to 10×). The example of detecting two colors with two transmission bands is not limiting, and more than two colors can be detected by interleaving additional micro-filters having other transmission bands. In still another embodiment, the fluorescence signal of two fluorescent proteins are recorded in sequence on a single image sensor 6. In such a configuration, light sources 5A corresponding to each fluorescent marker are turned on/off in a sequence synchronized with the acquisition rate of image sensor 6. In one example, GCaMP6 fluorescent proteins having emission of approximately 515 nm may be excited by an illumination wavelength of approximately 480 nm, while RCaMP1 fluorescent proteins having an emission wavelength of approximately 600 nm are excited with an illumination wavelength around 565 nm. In another example, a third light source 5A at the isosbestic wavelength of the calcium indicator is added to the system for control measurements (e.g. around 405 nm for GCaMP6).

Figure 5B:
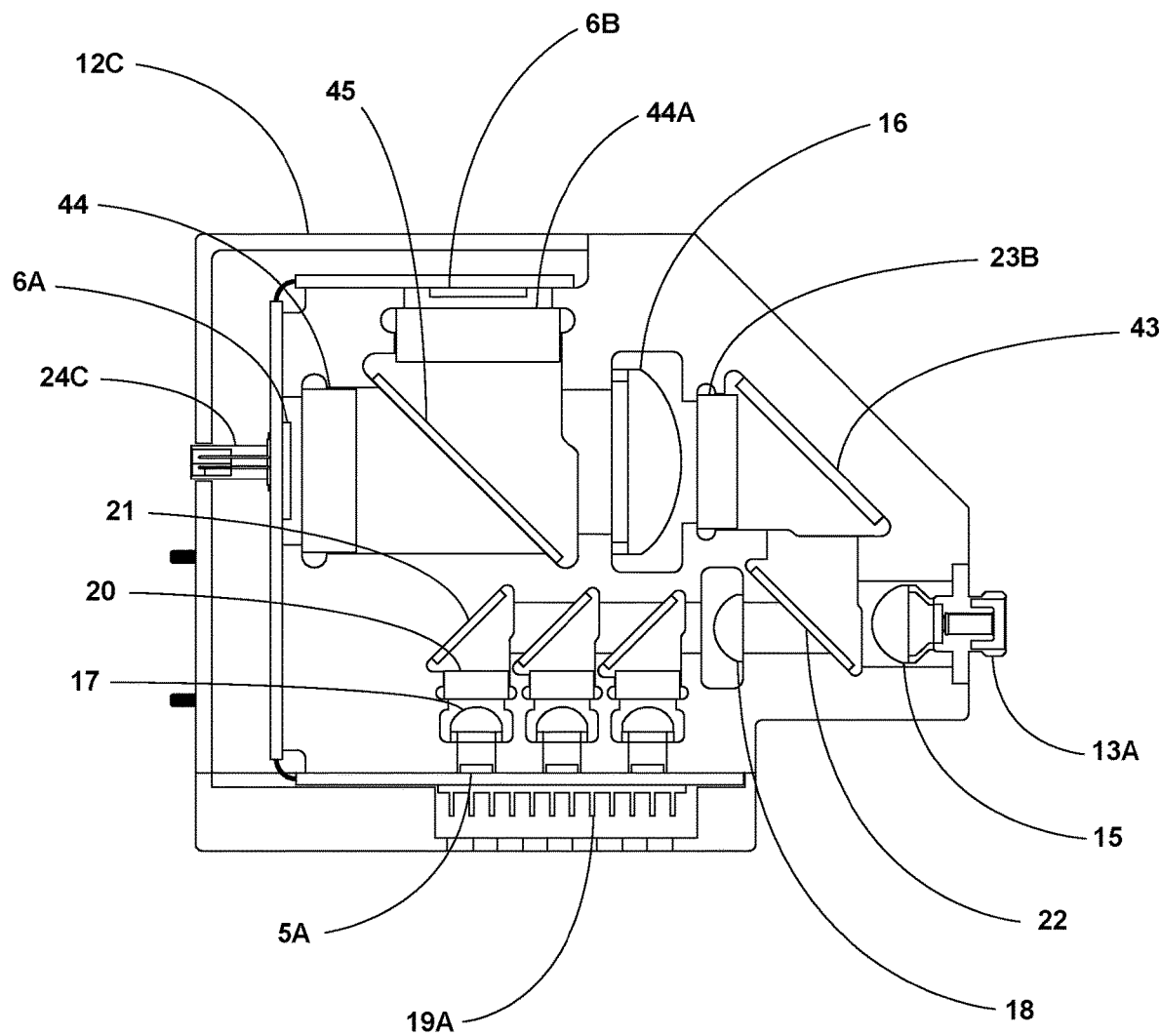
FIG. 5B is a side cut-away view of an alternative fluorescence stimulation/detection unit 12C that may be used in electrical rotary joint 130A of FIG. 3 and FIG. 4.

Referring now to FIG. 5B, a cut-away side view of an alternative fluorescence stimulation/detection unit 12C that may be used in place fluorescence stimulation/detection unit 12A of FIG. 5A of is shown, illustrating details of the optical and electrical components within. Fluorescence stimulation/detection unit 12C of FIG. 5B is similar to fluorescence stimulation/detection unit 12A of FIG. 5A, so only differences between them will be described below. Two image sensors 6A and 6B are provided in fluorescence stimulation/detection unit 12C and an additional (second) dichroic beamsplitter 45 is included to separate light of different wavelengths between sensors 6A and 6B, which provide separate image sensor outputs to data acquisition and control unit 2 of FIG. 1A via an electrical connector 24C. A dual-band emission filter 23B removes stray light coming from excitation light reflections within fluorescence stimulation/detection unit 12C. Dichroic beamsplitter 22 separates the fluorescence measurement signals from the excitation illumination and second dichroic beamsplitter 45 separates the two fluorescence signals emitted by the two fluorescent markers. Image sensors 6A,6B each include a single band emission filter 44, 44A, that removes stray excitation light from excitation light reflections within fluorescence stimulation/detection unit 12C, and also the fluorescence measurement signal from the other markers. Fluorescence stimulation/detection unit 12A is configured to image a field of view of up to 3 mm×3 mm on each of image sensors 6A, 6B, e.g., a CMOS or CCD sensor, with 1 to 10× magnification. The size of the field of view limits the number of brain regions that can be monitored simultaneously. In interface 25A of FIG. 2A, the proximal end of seven optical fibers 400 microns in diameter are imaged simultaneously on both of image detectors 6A,6B. In an example application, the fluorescence measurement signal of two fluorescent proteins are recorded separately and simultaneously on image sensors 6A,6B. Single-band emission filters 44,44A are single band filters centered on the fluorescence emission of each fluorescent marker.

Figure 8:
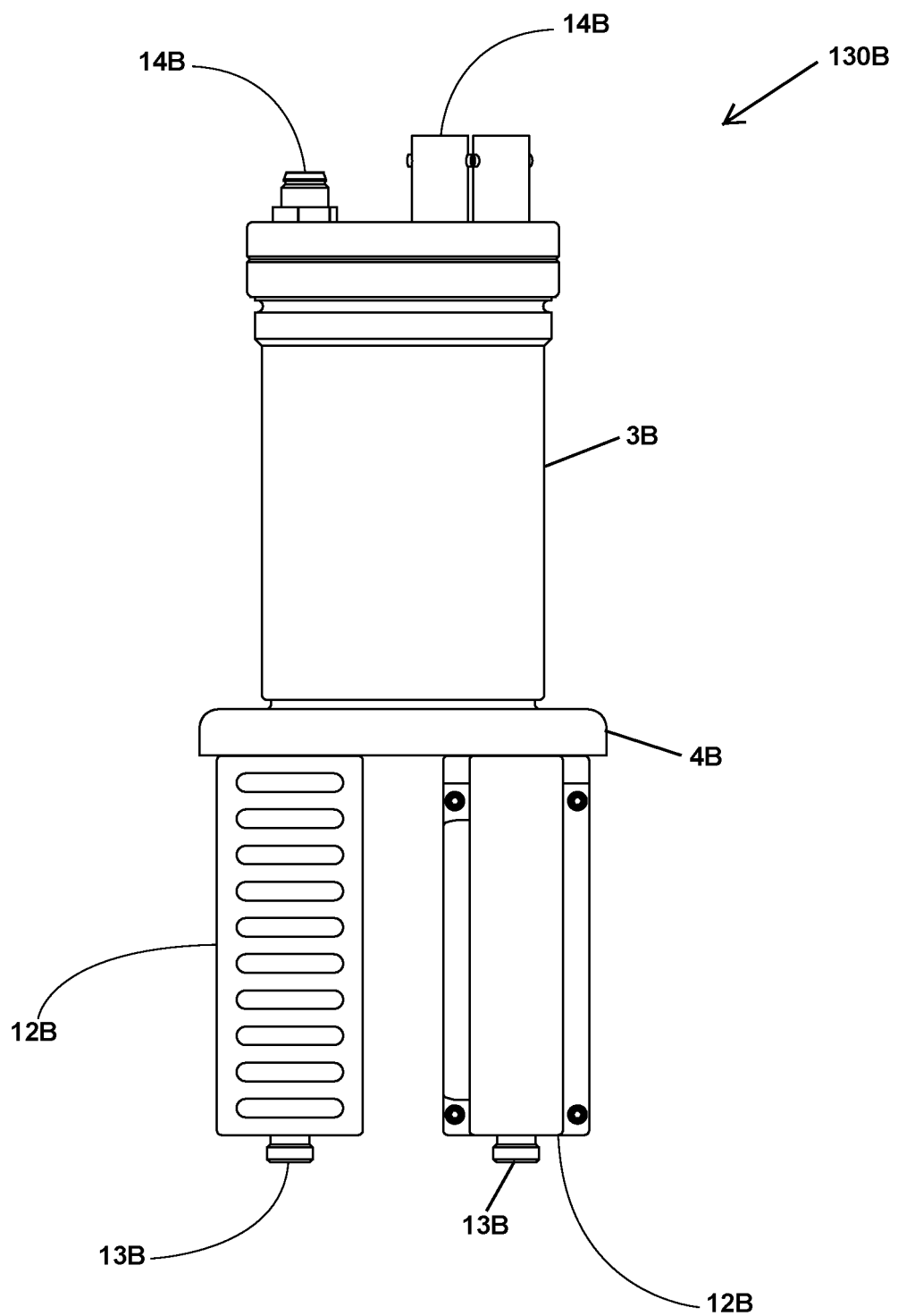
FIG. 8 is a side view of an example electrical rotary joint 130B of optical measurement system 100B of FIG. 1B.
Figure 9A:
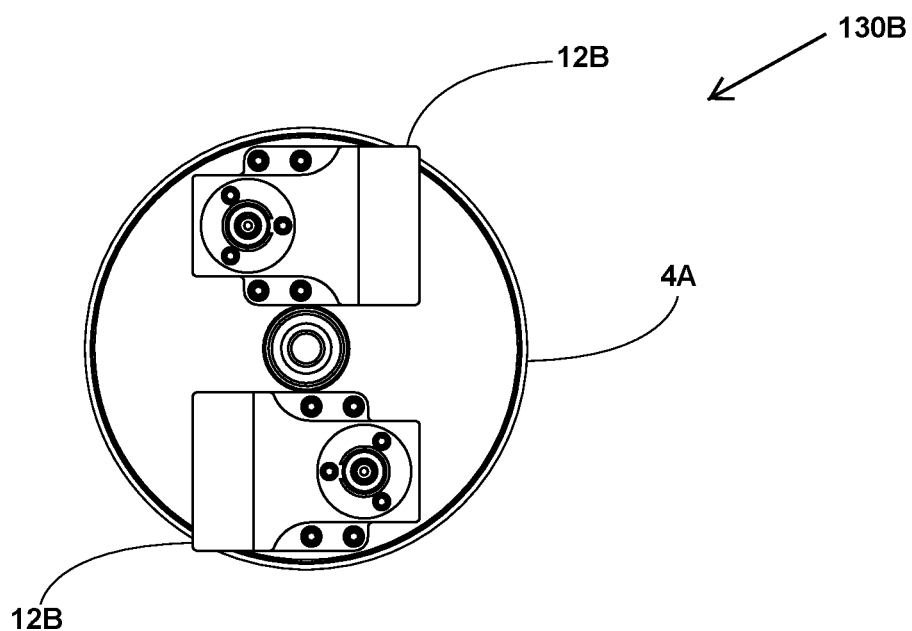
FIG. 9A is a bottom view of example electrical rotary joint 130B of FIG. 8.
Figure 9B:
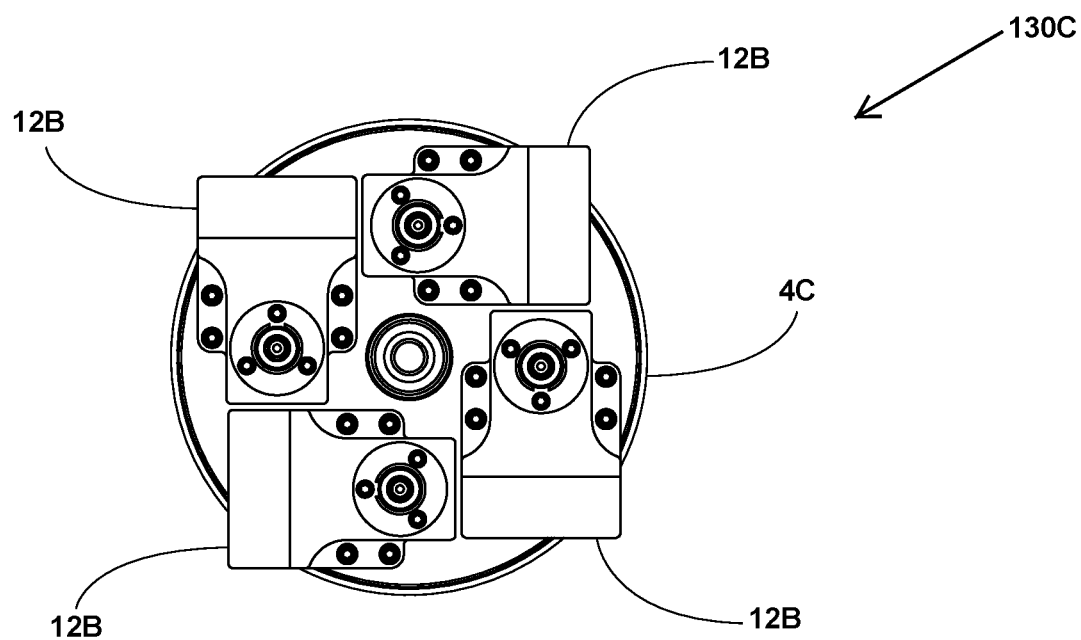
FIG. 9B is a bottom view of another example electrical rotary joint 130C that may be used within optical measurement system 100B depicted in FIG. 1B.
Figure 9C:
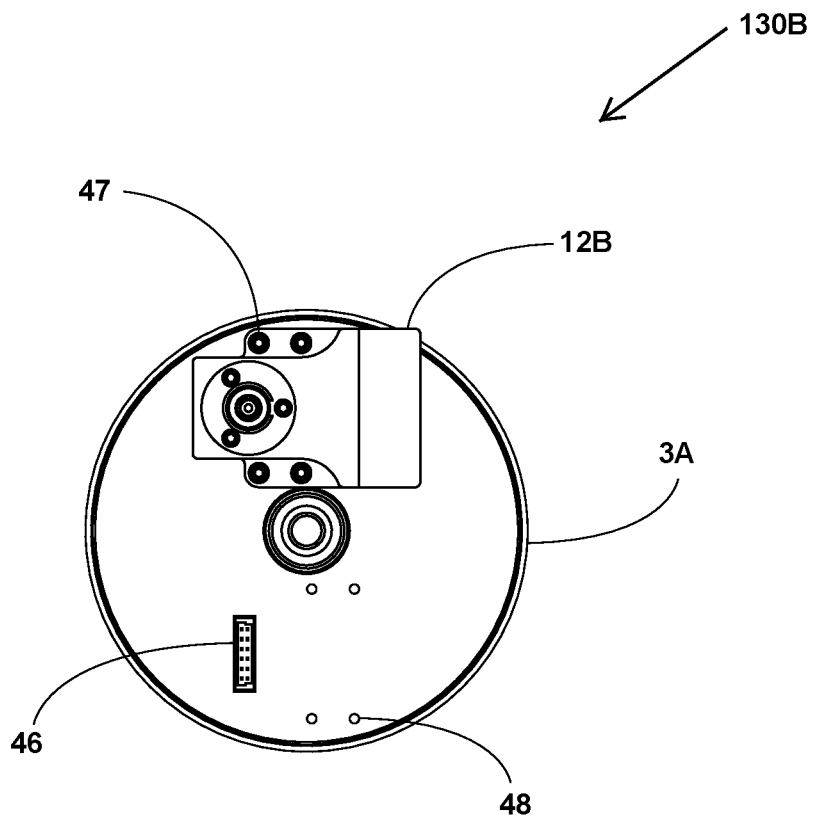
FIG. 9C is of example electrical rotary joint 130B of FIG. 8 with one of fluorescence stimulation/detection units 12B removed.

Referring now to FIG. 8 and FIG. 9A, a side view and a bottom view, respectively, of electrical rotary joint 130B of optical measurement system 100B of FIG. 1B are shown. The positions of rotor 4B and stator 3B are shown, and rotor 4B is rotationally coupled to stator 3B with a low-friction bearing and electrical interconnects. Electrical connections 14B are provided on stator 3B for connection to data acquisition and control unit 2 of FIG. 1B. Two fluorescence stimulation/detection units 12B are mounted to, or form the body of rotor 4B, which includes connectors 13B for attachment of connectors 26B of multiple instances of fiber optic cable 8B of FIG. 2B. FIG. 9B shows an alternative embodiment in which four fluorescence stimulation/detection units 12B are mounted to, or form the body of rotor 4C of an electrical rotary joint 103C. FIG. 9C shows a bottom view of electrical rotary joint 130B of FIG. 9A with one of fluorescence stimulation/detection units 12B removed, exposing mounting holes 48 through which machine bolts 47 are inserted to mount fluorescence stimulation/detection units 12B and an electrical connector 46 that connects to electrical connectors 24A,24B of fluorescence stimulation/detection units 12B (or 12A) to provide power for light sources 5A and receive the fluorescence detection signals from photo-detectors 10 or image sensor 6.

Figure 10:
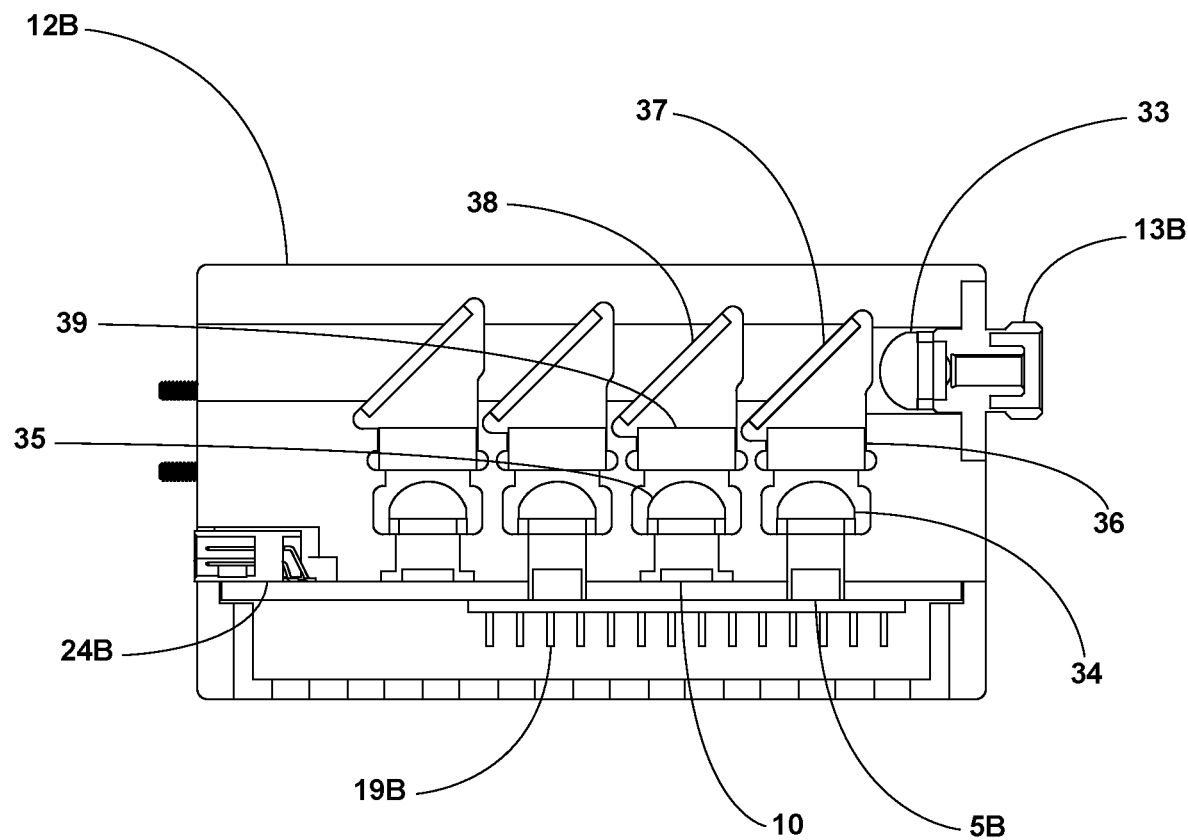
FIG. 10 is a side cut-away view of a fluorescence stimulation/detection unit 12B of electrical rotary joint 130B of FIG. 8.

Referring now to FIG. 10, a cut-away side view of an individual one of fluorescence stimulation/detection units 12B is shown, illustrating details of the optical and electrical components within. Fluorescence stimulation/detection units 12B are similar to fluorescence stimulation/detection units 12A of FIG. 5A, so only differences between them and the associated applications are discussed in detail below. Connector 13B, which receives one connector 26B of one of fiber optic cables 8B of FIG. 2B and interface 25B thereby, is optically coupled by an objective lens 33. Fluorescence stimulation/detection units 12B are configured to image a single optical fiber at interface 25B of up to 1 mm in diameter. The advantage of using single point photo-detectors 10, instead of image sensors 6 as in fluorescence stimulation/detection unit 12A of FIG. 5A, are higher detection bandwidth and higher sensitivity. To simultaneously record the activity of multiple brain regions, optical measurement system 100B of FIG. 1B requires one complete fluorescence stimulation/detection unit 12B per fiber optic cable 8B, limiting the maximum number of brain regions that can be recorded. An electrical connector 24B provides for electrical connections between rotor 4A and each of fluorescence stimulation/detection units 12B, providing power/control for light sources 5B, as well as an interface to a photo-detector 10 within fluorescence stimulation/detection unit 12A. Since optical power requirements for fiber-photometry measurement are low, the heat produced by light sources 5B is also low and the heat can be dissipated passively with a passive heat sink 19B. If higher thermal dissipation is required, a fan may be included to move air over the fins of heat sink 19B.

Figure 6B:
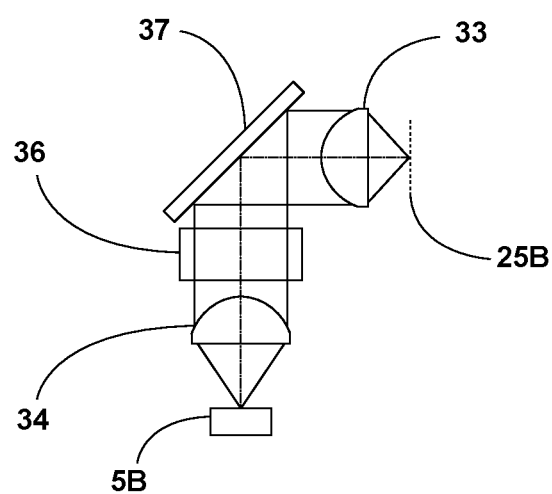
FIG. 6B is a pictorial diagram depicting an illumination pathway within fluorescence stimulation/detection unit 12B of FIG. 10.

Excitation light is provided by light sources 5B, e.g., LEDs or laser diodes, for fluorescence protein excitation. Each of the outputs of light sources 5B is first collimated by an aspheric lens 34 and then focused on interface 25B of the optical fiber of fiber optic cable 8B by objective lens 33. FIG. 6B, which is referred to additionally, illustrates the illumination pathway between each of light sources 5B and interface 25B of the optical fiber in the corresponding fiber optic cable 8B of FIG. 2B. An excitation bandpass filter 36 and a dichroic beamsplitter 37 included in optical filters 7B of FIG. 1B filter and direct excitation light from light sources 5B to objective lens 33. Objective lens 33 also collimates the returning fluorescence light received from interface 25B of fiber optic cable 8B, which may be an aspheric or multi-element lens, e.g., an achromatic doublet, in order to reduce the angle of incidence of the light incident on emission bandpass filter 39 and a dichroic beamsplitter 38 included in optical filters 7B of FIG. 1B that separate the excitation illumination path from the detection path, and thereby improve filtering efficiency. The collimated fluorescence measurement beam from objective lens 33 is then focused on each photo-detector 10 by a corresponding one of focusing lenses 35, which in the example may be another aspheric lens. In the example, the numerical aperture of both objective lens 33 and focusing lenses 35 is between 0.20 and 0.80.

In fluorescence stimulation/detection unit 12B as illustrated in FIG. 10, two sets of excitation bandpass filters 36 and dichroic beamsplitters 37 are shown that form a primary filter set that separates the excitation illumination from the detection optical pathway. However, the number of excitation sources, i.e., light sources 5B may be from a single light source 5B up to the limits of module size that can be provided on rotor 4B and any degradation of the excitation illumination pathway through the multiple dichroic beamsplitters 37, 38. The primary filter set is configured to combine excitation illumination light from one, two, or three light sources 5B, which in the example of FIG. 10 is two. The primary filter set features: an individual excitation bandpass filter 36 for each light source 5B that reduces the spectral bandwidth of the illumination lights, and an individual dichroic beamsplitter 37 for each light source 5B to combine two or three bands of excitation lights in a single excitation pathway. A secondary filter set separates the one, two or three bands of fluorescence signals emitted by the sample from one, two or three bands of excitation lights. The secondary filter set varies according to number and type of fluorescent markers to be detected.

In one example embodiment, the returning fluorescence measurement signal of one fluorescent protein is detected by photo-detector 10, and one light source 5B is used for excitation. In such a configuration, a filter set includes a first dichroic beamsplitter 37 for light source 5B that reflects the excitation light from each of light sources 5B to connector 13B, an excitation band-pass filter 36 and an aspheric lens 34 for light source 5B, a second dichroic beamsplitter 38 that separates the returning fluorescence measurement signal for photo-detector 10, and detection band-pass filter 39 having a pass-band centered on the emission wavelength of the fluorescent marker that removes stray light coming from excitation light reflections within fluorescence stimulation/detection unit 12B. As mentioned above, a second excitation light source 5B at the isosbestic wavelength of the calcium indicator may be added to the system for control measurements, e.g., approximately 405 nm for GCaMP6.

In another example multi-color configuration, the fluorescence measurement signal of multiple markers having two different excitation and emission spectra are recorded simultaneously by providing one light source 5B and one photo-detector 10 for each marker. As in the single-color example given above, the filter set includes first dichroic beamsplitter 37 for each of light sources 5B that reflects the excitation light from each of light sources 5B to connector 13B, an individual excitation band-pass filter 36 for each of light sources 5B, a second dichroic beamsplitter 38 for each photo-detector 10 that separates the returning fluorescence measurement signal for each photo-detector 10, and individual detection band-pass filter 39 for each photo-detector. Detection band-pass filter 39 has a pass-band centered on the emission wavelength of the corresponding fluorescent marker that removes stray light coming from excitation light reflections within fluorescence stimulation/detection unit 12B, and also the fluorescence measurement signal from the other markers. To minimize lead of excitation light reflections directly to photo-detectors 10, it is important to avoid spectral overlap between the pass-bands of excitation band-pass filter 36 and detection band-pass filter 39.

Figure 11:
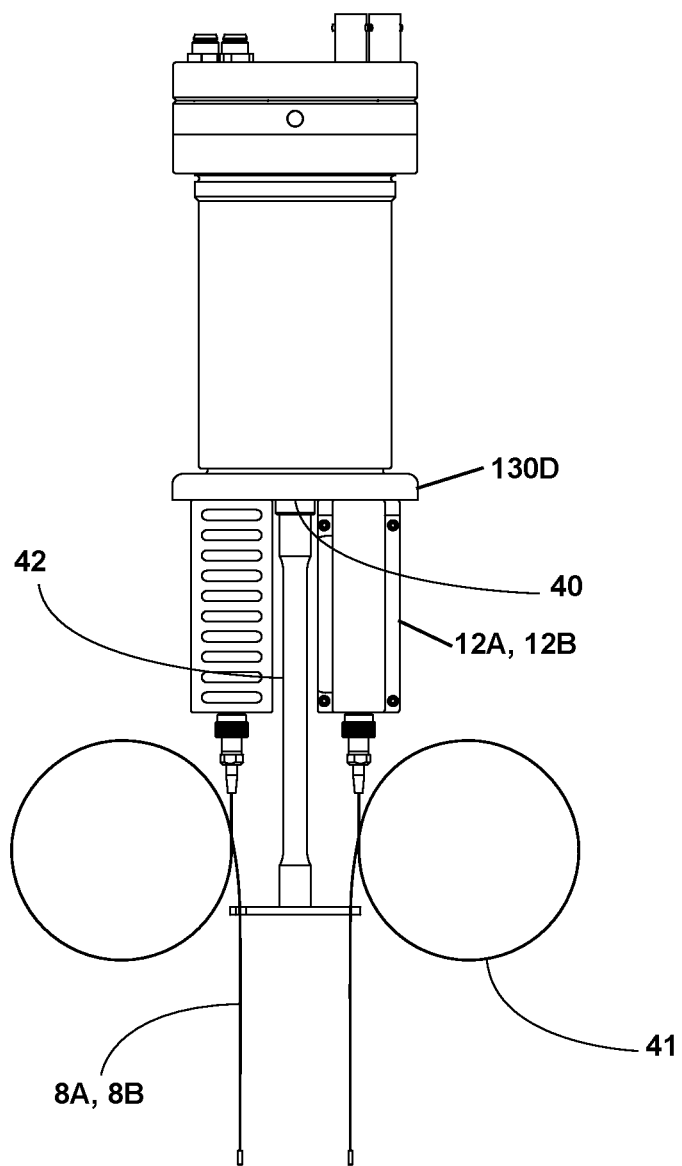
FIG. 11 is a side view of an example of optical measurement system 100B of FIG. 1B, including a motor-assisted electrical rotary joint 130D.

As mentioned above, electrical rotary joints 130A and 130B of FIG. 3 and FIG. 8, respectively are generally low-friction rotary joints having low-friction electrical connections, e.g., liquid metal, magnetic transmission, slip rings, etc. In one embodiment, the rotary joints 130A, 130B passively follows movement of sample 9. Referring now to FIG. 11, in another embodiment designed for small rodents, fiber optic cables 8A in optical measurement system 100A of FIG. 1A, or fiber optic cables 8B in optical measurement system 100B of FIG. 1B, are mechanically coupled to a torque sensor 40 by a guide 42 that rotates independently from electrical rotary joint 130D. Torque sensor 40 triggers motor-assisted rotation of an electrical rotary joint 130D that includes a motor, resulting in friction-free rotation when fiber optic cables 8A,8B rotate guide 42. The proximal ends of fiber optic cables 8A, 8B are connected to fluorescence stimulation/detection units 12A or 12B disposed on electrical rotary joints 130A, 130B. To maintain sufficient torque sensing, fiber optic cables 8A, 8B are formed in loops 41 between guide 42 and fluorescence stimulation/detection units 12A, 12B.

While the invention has been particularly shown and described with reference to the preferred embodiment thereof, it will be understood by those skilled in the art that the foregoing and other changes in form, and details may be made therein without departing from the spirit and scope of the invention.

What is claimed:

1. An optical measurement system for simultaneously making multiple fluorescence measurements at multiple distinct regions within a moving sample, the system comprising:
a plurality at optical fibers having first ends coupled to the moving sample;
an electrical rotary joint, the electrical rotary joint including a rotor and a stator, wherein the rotor includes at least one optical connection for receiving second ends of the plurality of optical fibers, and at least one fluorescence stimulation/detection unit coupled to the at least one optical connection for introducing excitation light to the plurality of optical fibers and receiving returning fluorescence light from the plurality of optical fibers, wherein the at least one stimulation/detection unit comprises at least one light source for generating the excitation light, at least one optical multiplexing filter optically coupled to the at least one optical connection and the at least one light source for separating the returning fluorescence light from the excitation light, and at least one electro-optical detector coupled to the at least one optical connection for detecting the returning fluorescence light, wherein an a first electrical signal output of the at least one electro-optical detector is coupled from the rotor to the stator, and wherein the stator provides at least one electrical output coupled to the first electrical signal for providing electrical connection to the at least one electro-optical detector, and wherein an electrical input of the at least one light source is coupled from the rotor to the stator as a second electrical signal; and
a data acquisition and control unit having one or more electrical detection inputs coupled to the at least one electrical output of the stator of the electrical rotary joint for recording a corresponding one of the at least one output of the at least one electro-optical detector and at least one electrical output coupled to at least one electrical input of the stator for controlling power supplied to the input of a corresponding one of the at least one light source.

2. The optical measurement system of claim 1, wherein the at least one electro-optical detector is at least one image sensor, wherein the second ends of the plurality of optical fibers are optically coupled to corresponding ones of a plurality of regions of a field-of-view of the at least one image sensor.

3. The optical measurement system of claim 2, wherein the at least one fluorescence stimulation/detection unit includes multiple light sources for providing selectable wavelengths of the excitation light, and wherein the at least one fluorescence stimulation/detection unit further comprises at least one separation filter for separating the returning fluorescence light into multiple emissions of multiple wavelengths of the sample corresponding to the selectable wavelengths of the excitation light and that directs components of the separated returning fluorescence light to different pixel sets in the corresponding ones of the plurality of regions of the field-of-view of the at least one image sensor.

4. The optical measurement system of claim 2, wherein the at least one fluorescence stimulation/detection unit is a single fluorescence stimulation/detection unit, and wherein the at least one optical connection is a single connection at which the second ends of the at least one of the plurality of optical fibers are combined to provide an image input to the single fluorescence stimulation/detection unit.

5. The optical measurement system of claim 4, wherein the single fluorescence stimulation/detection unit comprises:
   an objective lens that receives the image input and couples light from the at least one light source to the second ends of the plurality of optical fibers;
   the at least one light source;
   the at least one optical multiplexing filter; and
   a housing that incorporates the objective lens, the at least one light source, the at least one optical multiplexing filter and provides the at least one optical connection at an exterior surface of the housing.

6. The optical measurement system of claim 5, further comprising:
   a collimating lens for collimating light from the at least one light source; and
   a focusing lens for focusing collimated light from the collimating lens on a back focal plane of the objective lens, so that the second ends of the plurality of optical fibers receive uniform illumination from each of the at least one light source.

7. The optical measurement system of claim 2, wherein the at least one image sensor comprises a first image sensor and a second image sensor, wherein the second ends of the at least one of the plurality of optical fibers are optically coupled to corresponding ones of a plurality of regions of a field-of-view of both the first image sensor and the second sensor, and wherein the optical measurement system further comprises a dichroic beamsplitter that separates the returning fluorescence light according to wavelength and directs corresponding wavelengths of the separated returning fluorescence light to the first image sensor and to the second image sensor.

8. The optical measurement system of claim 2, wherein the at least one image sensor is a single image sensor, wherein the at least one light source comprises multiple light sources, and wherein the a data acquisition and control unit controls a sequence of fluorescence measurements that activates individual ones of the multiple light sources in sequence and collects measurement data from the at least one image sensor in response to activating each individual one of the multiple light sources, in to collect data for different excitation wavelengths of the sample.

9. The optical measurement system of claim 1, wherein the at least one optical connection is a plurality of optical connections, wherein the at least one fluorescence stimulation/detection unit comprises a plurality of fluorescence stimulation/detection units corresponding to the plurality of optical connections, whereby each of the plurality of fluorescence stimulation/detection units introduces corresponding excitation light and receives returning fluorescence light from a corresponding one of the plurality of optical fibers.

10. The optical measurement system of claim 9, wherein the at least one fluorescence stimulation/detection unit includes multiple light sources for providing selectable wavelengths of the excitation light, wherein the at least one electro-optical detector comprises multiple electro-optical detectors for detecting wavelengths of the returning fluorescence light corresponding to the selectable wavelengths of the excitation light, and wherein the at least one fluorescence stimulation/detection unit further comprises at least one separation filter for separating the returning fluorescence light into the multiple emissions of multiple wavelengths of the sample corresponding to the selectable wavelengths of the excitation light and that directs components of the separated returning fluorescence light to corresponding ones of the multiple electro-optical detectors.

11. The optical measurement system of claim 10, wherein the plurality of fluorescence stimulation/detection units each comprise:
   an objective lens that receives the returning fluorescence light from a second end of the corresponding one of the plurality of optical fibers and couples light from the at least one light source to the second end of the corresponding one of the plurality of optical fibers;
   the at least one light source;
   the at least one optical multiplexing filter; and
   a housing that incorporates the objective lens, the at least one light source, the at least one optical multiplexing filter, and the at least one electro-optical detector, and provides a corresponding one of the at least one optical connection at an exterior surface of the housing.

12. The optical measurement system of claim 9, wherein the light from the at least one light source is focused by the objective lens on the second ends of corresponding ones of the plurality of optical fibers.

13. The optical measurement system of claim 12, further comprising a collimating lens that collimates the light from the at least one light source before the light from the at least one light source is focused by the objective lens.

14. The optical system of claim 1, wherein the electrical rotary joint further comprises:
   a motor for rotating the rotor with respect to the stator; and
   a torque sensor mechanically coupled to the rotor and the stator for detecting a rotational force applied to the rotor by the moving sample, and wherein a control unit of the optical measurement system is coupled to the torque sensor and the motor to activate the motor in response to detecting the rotational force.

15. The optical system of claim 1, wherein the at least one fluorescence stimulation/detection unit is an interchangeable module providing for substitution of another fluorescence stimulation/detection unit having differing detection and excitation wavelength capabilities.

16. An optical measurement system for simultaneously making multiple fluorescence measurements at multiple distinct regions within a moving sample, the system comprising:
   a plurality of optical fibers having first ends coupled to the moving sample;
   an electrical rotary joint, the electrical rotary joint including a rotor and a stator, wherein the rotor includes at least one optical connection for receiving a bundle of second ends of the plurality of optical fibers as an image input, and a fluorescence stimulation/detection unit coupled to the at least one optical connection for introducing excitation light to the plurality of optical fibers and receiving returning fluorescence light from the plurality of optical fibers, wherein the stimulation/detection unit comprises an objective lens that receives the image input and couples light from the at least one light source to the second ends of the plurality of optical fibers, multiple light sources for generating the excitation light at selectable wavelengths, at least one optical multiplexing filter optically coupled to the at least one optical connection and the at least one light source for separating the returning fluorescence light from the excitation light, wherein the light from the at least one light source is collimated by a collimating lens, wherein collimated light from the collimating lens is focused by a focusing lens at the back focal plane of the objective lens, so that the second ends of the plurality of optical fibers receive uniform illumination from each of the at least one light source, and at least one image sensor coupled to the at least one optical connection for detecting the returning fluorescence light, wherein the second ends of plurality of optical fibers are optically coupled to corresponding ones of a plurality of regions of a field-of-view of the image sensor, a separation filter for separating the returning fluorescence light into multiple emissions of multiple wavelengths of the sample corresponding to the selectable wavelengths of the excitation light and directs components of the separated returning fluorescence light to corresponding different pixel sets of the corresponding ones of the plurality of regions of the field-of-view of the at least one image sensor, a housing that incorporates the objective lens, the at least one light source, the at least one optical multiplexing filter, and the at least one separation filter, and provides the at least one optical connection at an exterior surface of the housing, wherein an electrical signal output of the at least one image sensor is coupled from the rotor to the stator, and wherein the stator provides at least one electrical output coupled to the first electrical signal for providing electrical connection to the at least one electro-optical detector, and wherein an electrical input of the at least one light source is coupled from the rotor to the stator as a second electrical signal; and a data acquisition and control unit having one or more electrical detection inputs coupled to the at least one electrical output of the stator of the electrical rotary joint for recording an output of the at least one image sensor and having at least one output for controlling power supplied to the input of a corresponding one of the at least one light source.

17. An optical measurement system for simultaneously making multiple fluorescence measurements at multiple distinct regions within a moving sample, the system comprising:

a plurality of optical fibers having first ends coupled to the moving sample;

an electrical rotary joint, the electrical rotary joint including a rotor and a stator, wherein the rotor includes multiple optical connections for receiving second ends of the plurality of optical fibers and a corresponding plurality of fluorescence stimulation/detection units coupled to corresponding ones of the multiple optical connections for introducing excitation light to the plurality of optical fibers and receiving returning fluorescence light from the plurality of optical fibers, wherein the plurality of fluorescence stimulation/detection units each comprise multiple light sources for generating the excitation light for providing selectable wavelengths of the excitation light, multiple photo-detectors for detecting wavelengths of the returning fluorescence light corresponding to the selectable wavelengths of the excitation light, at least one separation filter for separating the excitation light from the returning fluorescence light and for separating the returning fluorescence light into the multiple emissions of multiple wavelengths of the sample corresponding to the selectable wavelengths of the excitation light and directing components of the separated returning fluorescence light to corresponding ones of the multiple photo-detectors, at least one optical multiplexing filter optically coupled to the multiple optical connections and the multiple light sources for separating the returning fluorescence light from the excitation light and directing the excitation light from the multiple light sources to the corresponding one of the multiple optical connections, wherein corresponding ones of the at multiple photo-detectors are coupled to the corresponding one of the multiple optical connections for receiving the returning fluorescence light from a corresponding one of the plurality of optical fibers, wherein outputs of the multiple photo-detectors are coupled from the rotor to the stator as at least one first electrical signal, and wherein the stator provides electrical outputs for providing electrical connection to the multiple photo-detectors, and wherein an electrical input of the at least one light source is coupled from the rotor to the stator as at least one second electrical signal; and a data acquisition and control unit having one or more electrical detection inputs coupled to the electrical outputs of the stator of the electrical rotary joint for recording an output of the multiple photo-detectors and at least one output for controlling power supplied to the input of a corresponding one of the at least one light source.

18. A method of simultaneously making multiple fluorescence measurements at multiple distinct regions within a moving sample, the method comprising:

coupling first ends of a plurality of optical fibers to the moving sample;

stimulating fluorescence emissions of multiple regions within the moving sample while preventing twisting of the plurality of optical fibers by introducing excitation light to second ends of the plurality of optical fibers from at least one fluorescence stimulation/detection unit of a rotor of an electrical rotary joint;

detecting the fluorescence emissions from the multiple regions from the second ends of the plurality of optical fibers with the at least one fluorescence stimulation/detection unit of the rotor, wherein at least one fluorescence stimulation/detection unit of the rotor includes at least one optical connection for receiving second ends of the plurality of optical fibers, wherein the at least one fluorescence stimulation/detection unit is coupled to the at least one optical connection for performing the introducing of the excitation light and the detecting of the returning fluorescence light from the plurality of optical fibers and includes at least one light source for generating the excitation light, at least one optical multiplexing filter optically coupled to the at least one optical connection and the at least one light source for separating the returning fluorescence light from the excitation light, and at least one electro-optical detector coupled to the at least one optical connection for performing the detecting of the returning fluorescence light;

coupling an electrical output of the at least one electro-optical detector from the rotor to a stator of the electrical rotary joint as a first electrical signal, wherein the stator provides at least one electrical output input for coupling to the first electrical signal providing an electrical connection to the at least one electro-optical detector;

coupling an electrical input of the at least one light source from the rotor to the stator as a second electrical signal; and recording an output of the at least one electro-optical detector and controlling power supplied to the input of the at least one light source by a data acquisition and control unit having one or more electrical detection inputs coupled to the at least one electrical output of the stator of the electrical rotary joint and at least one output coupled to the at least one electrical input of the stator of the electrical rotary joint.

19. The method of claim 18, wherein the detecting fluorescence emissions comprises detecting an image with at least one image sensor, wherein the image is an image of fluorescence emissions from a composite bundle of the second ends of the at least one of the plurality of optical fibers that are optically coupled to corresponding ones of a plurality of regions of a field-of-view of the at least one image sensor.

20. The method of claim 19, wherein the at least one light source comprises multiple light sources, and wherein the method further comprises:
    selecting wavelengths of the excitation light by activating one of more of multiple light sources;
    separating the returning fluorescence light into multiple emissions of multiple wavelengths of the sample corresponding to the selectable wavelengths of the excitation light with at least one separation filter of the at least one fluorescence stimulation/detection unit; and
    directing components of the separated returning fluorescence light to different pixel sets in the corresponding ones of the plurality of regions of the field-of-view of the at least one image sensor.

21. The method of claim 20, further comprising enclosing an objective lens that receives the image input and couples light from the at least one light source to the second ends of the plurality of optical fibers, the at least one light source, and the at least one optical multiplexing filter in a housing that provides the at least one optical connection at an exterior surface of the housing and is located within or mounted to the rotor.

22. The method of claim 21, wherein the introducing excitation light to second ends of the plurality of optical fibers images the light from the at least one light source on a back focal plane of the objective lens, so that the second ends of the plurality of optical fibers receive uniform illumination from each of the at least one light source.

23. The method of claim 19, wherein the at least one image sensor comprises a first image sensor and a second image sensor, wherein the method further comprises:
    separating the returning fluorescence light according to wavelength; and
    directing corresponding wavelengths of the separated returning fluorescence light to the first image sensor and to the second image sensor.

24. The method of claim 19, wherein the at least one image sensor is a single image sensor, wherein the at least one light source comprises multiple light sources, and wherein the method further comprises:
    activating individual ones of the multiple light sources in sequence; and
    in response to activating each individual one of the multiple light sources, collecting measurement data from the at least one image sensor in to collect data for different excitation wavelengths of the sample.

25. The method of claim 18, wherein the at least one optical connection is a plurality of optical connections, wherein the at least one fluorescence stimulation/detection unit comprises a plurality of fluorescence stimulation/detection units corresponding to the plurality of optical connections, wherein the introducing excitation light to second ends of the plurality of optical fibers is performed by each of the plurality of fluorescence stimulation/detection units introducing corresponding excitation light to corresponding ones of the plurality of optical fibers, and wherein the detecting is performed by receiving returning fluorescence light by each of the plurality of fluorescence stimulation/detection units receiving corresponding returning fluorescence light from the corresponding one of the plurality of optical fibers.

26. The method of claim 25, wherein the at least one fluorescence stimulation/detection unit includes multiple light sources, wherein the at least one electro-optical detector comprises multiple electro-optical detectors, and wherein the method further comprises:
    selecting wavelengths of the excitation light by activating one of more of multiple light sources;
    separating the returning fluorescence light into multiple wavelengths of multiple emissions of the sample corresponding to the selectable wavelengths of the excitation light with at least one separation filter of the at least one fluorescence stimulation/detection unit; and
    directing components of the separated returning fluorescence light to different ones of the multiple electro-optical detectors.

27. The method of claim 18, further comprising, for each of the plurality of fluorescence stimulation/detection units, enclosing an objective lens that receives the returning fluorescence light and couples light from the at least one light source to the second ends of the plurality of optical fibers, the at least one light source, and the at least one optical multiplexing filter in a housing that provides a corresponding one of the at least one optical connection at an exterior surface of the housing and is located within or mounted to the rotor.

28. The method of claim 18, further comprising substituting an interchangeable fluorescence stimulation/detection unit module for one of the at least one fluorescence stimulation/detection unit, wherein the interchangeable fluorescence stimulation/detection unit module has differing detection and excitation wavelength capabilities from the one of the at least one fluorescence stimulation/detection unit.

* * * * *